United States Patent [19]

Bugianesi et al.

[11] 4,229,441
[45] Oct. 21, 1980

[54] IMMUNOLOGIC ADJUVANT

[75] Inventors: Robert L. Bugianesi, Colonia; Mitree M. Ponpipom, Branchburg; Tsung-Ying Shen, Westfield, all of N.J.

[73] Assignee: Merck & Co., Inc., Rahway, N.J.

[21] Appl. No.: 965,559

[22] Filed: Dec. 1, 1978

[51] Int. Cl.³ .................... A61K 31/705; C07G 79/08
[52] U.S. Cl. ........................ 424/182; 536/5; 536/4
[58] Field of Search .................... 536/5, 122; 424/180, 424/182

[56] References Cited

U.S. PATENT DOCUMENTS

| | | | |
|---|---|---|---|
| 3,050,517 | 8/1962 | Hitchings et al. | 536/4 |
| 3,585,186 | 6/1971 | Conroy et al. | 536/5 |
| 3,752,803 | 8/1973 | Eberlein et al. | 536/5 |
| 4,096,247 | 6/1978 | Lantos | 536/122 |

*Primary Examiner*—Johnnie R. Brown
*Attorney, Agent, or Firm*—Donald J. Perrella; Julian S. Levitt

[57] ABSTRACT

Glycolipid compounds of the formulae

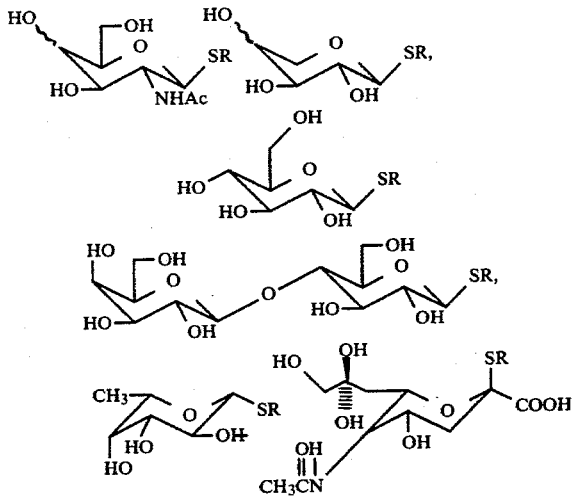

wherein R is

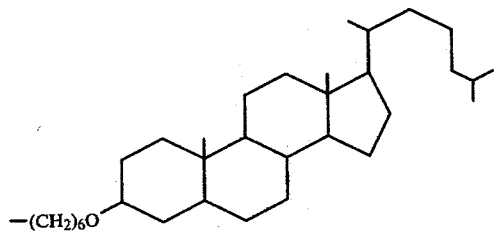

are useful immunologic adjuvants in vaccines.

4 Claims, No Drawings

IMMUNOLOGIC ADJUVANT

BACKGROUND OF THE INVENTION

The present invention relates to an immunologic adjuvant and, more particularly to novel glycolipid immunologic adjuvant and to improved vaccine formulations containing a novel glycolipid immunologic adjuvant.

Broadly considered, the vaccines utilized at the present time are "fluid vaccines." The term "fluid vaccine" designates a suspension of an immunogenic or desensitizing agent in water or in a medium comprising a single, aqueous, liquid phase. The principal purpose for employment of an immunologic adjuvant is to achieve a more durable immunity of a higher level employing a smaller antigenic mass in a fewer number of doses than could be achieved by administration of the equivalent aqueous antigen. It may be noted that development of an immunologically satisfactory and pharmacologically acceptable adjuvant is a prime essential for the preparation of workable multivalent killed virus vaccines which are effective and practical in the prevention of viral, bacterial, mycoplasmal or rickettsial diseases.

OBJECTS OF THE INVENTION

It is an object of the present invention to provide new glycolipid compounds. Another object is to provide methods for preparing these glycolipid compounds. A further object is to provide vaccine compositions containing these glycolipid compounds. These and other objects of the present invention will be apparent from the following description.

SUMMARY OF THE INVENTION

Glycolipid compounds of the formulae

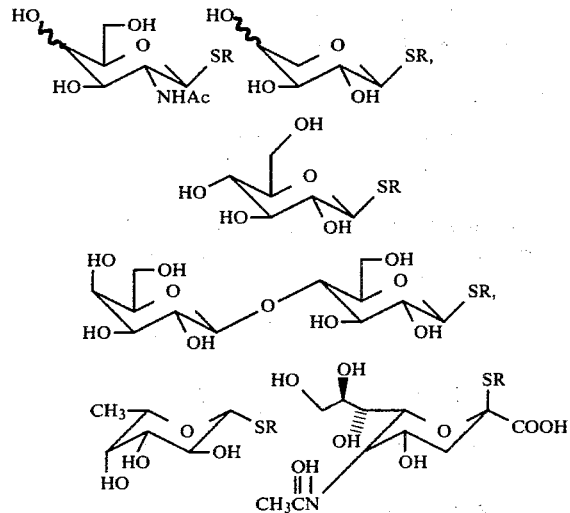

wherein R is

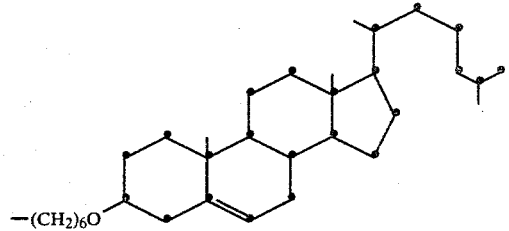

are useful immunologic adjuvants in vaccines.

DETAILED DESCRIPTION

The glycolipid compounds of the present invention which are useful as immunologic adjuvants are prepared starting from per-O-acetyl-1-thioglycopyranose and 6-(5-cholesten-3β-yloxy)hexyl iodide. Equimolar amounts of the foregoing compounds may be condensed in an inert, non-polar solvent such as a halogenated solvent, e.g., dichloromethane or chloroform in the presence of a base such as, e.g., triethylamine, 1,5-diazabicyclo[5.4.0]-undec-5-ene, or 1,5-diazabicyclo[4.3.0]-non-5-ene. The reaction may be carried out at from about 10° to about 30° C. under an inert atmosphere. Depending upon the base employed the reaction may take from about half an hour to about a few days. Thus, when employing 1,5-diazabicyclo[5.4.0]-undec-5-ene, or 1,5-diazabicyclo[4.3.0]-non-5-ene the reaction is usually completed in from about 0.5 to about 3 hours, while when employing triethylamine the reaction is usually completed in from about 1 to about 3 days. Following the reaction the solution is washed with water and dried if the solvent was a halogenated solvent, or if the solvent was tetrahydrofuran, the solution is evaporated to dryness and the residue is partitioned between dichloromethane and water. The dried solution is concentrated to a syrup which is put on a silica gel column and eluted with chloroform followed by 1–2% ethanol in chloroform. The desired fractions are pooled and evaporated to give the blocked product 6-(5-cholesten-3β-yloxy)hexyl per-O-acetyl-1-thioglycopyranoside which is deblocked by basic ion exchange treatment or sodium methoxide in methanol to give the desired final product.

The novel adjuvants of the invention may be employed to potentiate the antibody response of antigenic materials. The term "antigen" and "antigenic material" which are used interchangeably herein include one or more non-viable immunogenic or desensitizing (antiallergic) agents of bacterial, viral or other origin. The antigen component of the products of the invention may consist of a dried powder, an aqueous solution, an aqueous suspension and the like, including mixtures of the same, containing a non-viable immunogenic or desensitizing agent or agents.

The aqueous phase may conveniently be comprised of the antigenic material in a parenterally acceptable liquid. For example, the aqueous phase may be in the form of a vaccine in which the antigen is dissolved in a balanced salt solution, physiological saline solution, phosphate buffered saline solution, tissue culture fluids or other media in which the organism may have been grown. The aqueous phase also may contain preservatives and/or substances conventionally incorporated in vaccine preparations. The adjuvant emulsions of the invention may be prepared employing techniques well known to the art.

The antigen may be in the form of purified or partially purified antigen derived from bacteria, viruses, rickettsia or their products, or extracts of bacteria, viruses, or rickettsia, or the antigen may be an allergen such as pollens, dusts, danders, or extracts of the same or the antigen may be in the form of a poison or a venom derived from poisonous insects or reptiles. In all cases the antigens will be in the form in which their toxic or virulent properties have been reduced or destroyed and which when introduced into a suitable host will either induce active immunity by the production therein of antibodies against the specific microorganisms, extract or products of microorganisms used in the preparation of the antigen, or, in the case of allergens, they will aid in alleviating the symptoms of the allergy due to the specific allergen. The antigens can be used either singly or in combination for example, multiple bacterial antigens, multiple viral antigens, multiple mycoplasmal antigens, multiple rickettsial antigens, multiple bacterial or viral toxoids, multiple allergens or combinations of any of the foregoing products can be combined in the aqueous phase of the adjuvant composition of this invention. Antigens of particular importance are derived from bacteria such as *B. pertussis, Leptospira pomona* and *icterohaemorrhagiae, S. typhosa, S. paratyphi* A and B, *C. diphtheriae, C. tetani, C. botulinum, C. perfringens, C. feseri* and other gas gangrene bacteria, *B. anthracis, P, pestis, P. multocida, V. cholerae, Neisseria meningitidis, N, gonorrheae, Hemophilus influenzae, Treponema pollidum,* and the like; from viruses as polio virus (multiple types), adeno virus (multiple types), parainfluenza virus (multiple types), measles, mumps, respiratory syncytial virus, influenza (various types), shipping fever virus (SF4), Western and Eastern equine encephalomyelitis, Japanese B. encephalomyelitis, Russian Spring Summer encephalomyelitis, hog cholera virus, Newcastle disease virus, fowl pox, rabies, feline and canine distemper and the like viruses, from rickettsiae as epidemic and endemic typhus or other members of the spotted fever group, from various spider and snake venoms or any of the known allergens for example from ragweed, house dust, pollen extracts, grass pollens and the like.

The following examples illustrate the present invention without, however, limiting the same thereto. All temperatures are expressed in degrees celsius.

EXAMPLE 1

6-(5-Cholesten-3β-yloxy)hexyl 1-thio-β-L-fucopyranoside

A. 6-(5-Cholesten-3β-yloxy)hexyl 2,3,4-tri-O-acetyl 1-thio-β-L-fucopyranoside 2,3,4-Tri-O-acetyl-1-thio-β-L-fucopyranose (10 mmol) is treated with 6-(5-cholesten-3β-yloxy)hexyl iodide (10 mmol) in dichloromethane (30 ml) containing triethylamine (10 mmol). The reaction takes place in 1 day at room temperature under nitrogen. The resulting solution is washed with distilled water (20 ml) and dried with anhydrous sodium sulfate. The filtered solution is concentrated to form a syrup which is put on a silica gel column and eluted with chloroform followed by 1.0% ethanol in chloroform. The fractions containing the title compound, as determined by thin layer chromatography, are pooled and evaporated to give the title compound in 61% yield $[\alpha]_D$ $-4°$ (c 1.5, chloroform).

B. 6-(5-Cholesten-3β-yloxy)hexyl 1-thio-β-L-fucopyranoside

The blocked product from Step A is stirred with a basic ion exchange resin, Bio-Rad AG 1-X2 (OH), in ethanol-tetrahydrofuran or sodium methoxide in methanol to give the title compound as needles, yield 80%, m.p. 110°-112° (ethyl acetate), $[\alpha]_D$ $-11°$ (c 1.43, chloroform).

EXAMPLE 2

6-(5-Cholesten-3β-yloxy)hexyl 1-thio-β-D-glucopyranoside

A. 6-(5-Cholesten-3β-yloxy)hexyl 2,3,4,6-tetra-Oacetyl-1-thio-β-D-glucopyranoside The product of Example 1A is repeated except using 2,3,4,6-tetra-O-acetyl-1-thio-β-D-glucopyranose (10 mmol) in lieu of 2,3,4-tri-O-acetyl-1-thio-β-L-fucopyranose and using 1,5-diazabicyclo[5.4.0]-undec-5-ene (10 mmol) in lieu of triethylamine. The reaction takes place in 2 hours at room temperature under nitrogen. The title compound is obtained in 86% yield, m.p. 101°-102.5° (methanol), $[\alpha]_D$ $-36°$ (c 1.59, chloroform).

B. 6-(5-Cholesten-3β-yloxy)hexyl 1-thio-β-D-glucopyranoside

The title compound is obtained following the procedure of Example 1B, yield 62%, m.p. 110° (aqueous isopropanol), $[\alpha]_D$ $-41°$ (c 1.07, chloroform), $R_f$ 0.27 (chloroform-methanol, 9:1).

EXAMPLE 3

6-(5-Cholesten-3β-yloxy)hexyl 2-acetamido-2-deoxy-1-thioβ-D-glucopyranoside

A. 6-(5-Cholesten-3β-yloxy)hexyl 2-acetamido-3,4,6-tri-O-acetyl-2-deoxy-1-thio-β-D-glucopyranoside The procedure of Example 1 is repeated except using 2-acetamido-3,4,6-tri-O-acetyl-2-deoxy-1-thioβ-D-glucopyranose (10 mmol) in lieu of 2,3,4-tri-O-acetyl-1-thio-β-L-fucopyranose and using tetrahydrofuran (30 ml) in lieu of dichloromethane, and upon completion of the reaction, the mixture is evaporated to dryness and the residue partioned between dichloromethane (30 ml) and water (20 ml) and dried before forming the syrup which is put on the silica gel column. The title compound is obtained in 90% yield, m.p. 176°-179°, $[\alpha]_D$ $-43°$ (c 1.5, chloroform).

B. 6-(5-Cholesten-3β-yloxy)hexyl 2-acetamido-2-deoxy-1-thio-β-D-glucopyranoside

The title compound is obtained following the procedure of Example 1B, yield 77%, m.p. 183°-187° (dec) (methanol), $[\alpha]_D$ $-36°$ (c 1.5, dimethylsulfoxide), $R_f$ 0.48 (chloroform-methanol-water (80:20:2).

EXAMPLE 4

6-(5-Cholesten-3β-yloxy)hexyl 2-acetamido-2-deoxy-1-thio-β-D-galactopyranoside

A. 6-(5-Cholesten-3β-yloxy)hexyl 2-acetamido-3,4,6-tri-O-acetyl-2-deoxy-1-thio-β-D-galactopyranoside The procedure of Example 2A is repeated except using 2-acetamido-3,4,6-tri-O-acetyl-2-deoxy-1-thio-β-D-galactopyranose (10 mmol) in lieu of 2,3,4,6-tetra-O- acetyl-1-thio-β-D-glucopyranose. The title compound is obtained as a crystalline material, yield 43%, m.p. 130°-133° (ethanol), [α]$_D$ −37° (c 1.5, chloroform).

B. 6-(5-Cholesten-3β-yloxy)hexyl 2-acetamido-2-deoxy1-thio-β-D-galactopyranoside The title compound is obtained folllowing the procedure of Example 1B, yield 85%, m.p. 241°-243°, [α]$_D$ −35° (c 1.5, N,N-dimethylformamide).

EXAMPLE 5

6-(5-Cholesten-3β-yloxy)hexyl 1-thio-β-D-xylopyranoside

A. 6-(5-Cholesten-3β-yloxy)hexyl 2,3,4-tri-O-acetyl-1thio-β-D-xylopyranoside

The procedure of Example 2A is repeated except using 2,3,4-tri-O-acetyl-1-thio-β-xylopyranose in lieu of 2,3,4,6-tetra-O-acetyl-1-thio-β-D-glucopyranose. The title compound is obtained in 65% yield, m.p. 106°-108° (methanol), [α]$_D$ −56° (C 1.55, chloroform).

B. 6-(5-Cholesten-3β-yloxy)hexyl 1-thio-β-D-xylopyranoside

The title compound is obtained as a crystalline material following the procedure of Example 1B, m.p. 115° (methanol), [α]$_D$ −45° (c 1.47,

EXAMPLE 6

6-(5-Cholesten-3β-yloxy)hexyl 1-thio-α-L-arabinopyranoside

A. 6-(5-Cholesten-3β-yloxy)hexyl 2,3,4-tri-O-acetyl1-thio-α-L-arabinopyranoside

The procedure of Example 2A is repeated except using 2,3,4-tri-O-acetyl-1-thio-α-L-arabinopyranose (10 mmol) in lieu of 2,3,4,6-tetra-O-acetyl-1-thio-β-D-glucopyranose. The title compound is obtained in 64% yield, [α]$_D$ −22° (c 1.88, chloroform).

B. 6-(5-Cholesten-3β-yloxy)hexyl 1-thio-α-L-arabinopyranoside

The title compound is obtained following the procedure of Example 1B, yield 83%, [α]$_d$ −18° (c 2.0, chloroform).

EXAMPLE 7

6-(5-Cholesten-3β-yloxy)hexyl 1-thio-β-lactoside

A. 6-(5-Cholesten-3β-yloxy)hexyl hepta-O-acetyl-1-thio-β-lactoside

The procedure of Example 2A is repeated except using hepta-O-acetyl-1-thio-β-lactose (10 mmol) in lieu of 2,3,4,6-tetra-O-acetyl-1-thio-β-D-glucopyranose. The title compound is obtained in 46% yield, [α]$_D$ −22° (c 1.55 chloroform).

B. 6-(5-Cholesten-3β-yloxy)hexyl 1-thio-β-lactoside

The title compound is obtained as a crystalline material following the procedure of Example 1B, m.p. 189°-192° (aqueous isopropanol), [α]$_D$ −21° (c 1.63, dimethylsulfoxide), R$_f$ 0.26 (chloroform-methanol-water, 80:20:2).

EXAMPLE 8

2-S-[6-(5-Cholesten-3β-yloxy)hexyl]-2-thio-β-D-N-acetylneuraminic acid

A. 6-(5-Cholesten-3β-yloxy)-hexane-1-thiol

Thiourea (7.5 g) is added to a solution of 6-(5-cholesten-3β-yloxy)hexyl iodide (15 g, 25.3 mmol) in tetrahydrofuran (200 ml) and the mixture is heated with stirring under reflux for 6 hours. The solution is concentrated to a residue which is triturated with anhydrous ether. The solid is filtered and dissolved in chloroform (100 ml). This solution is added to a solution of potassium metabisulfite (15 g) in water (100 ml). The mixture is heated under reflux in a nitrogen atmosphere for 20 minutes. The organic layer is washed with water, dried, and concentrated to dryness. The crude material is put on a silica gel column and eluted with 5% ethyl ether in peteroleum ether. The dried fractions are pooled and concentrated to give the title compound (11 g, 86% yield), m.p. 89°-90°.

B. Methyl 4,7,8,9-tetra-O-acetyl-N-acetyl-2-S-[6-(5-cholesten-3β-yloxy)hexyl]-2-thio-D-neuraminate Boron trifluoride etherate (700 µl, 5.5 mmol) is added to a solution of methyl 2,4,7,8,9-penta-O-acetyl-N-acetyl-D-neuraminate (1.01 g, 1.96 mmol) and 6-(5-cholesten-3β-yloxy)-hexane-1-thiol (0.98 g, 1.96 mmol) in dry chloroform (5 ml). The mixture is stirred under nitrogen for 5 hours at room temperature, and washed with aqueous sodium bicarbonate and water. The dried solution is concentrated to a residue which is put on a silica gel column and eluted with chloroform-ethyl ether-methanol (31:10:1). The β-anomer is isolated as a glass (400 mg), [α]$_D$ −38.5° (c 1.5, chloroform).

C. 2-S-[6-(5-Cholesten-3β-yloxy)hexyl]-2-thio-β-D-N-acetylneuraminic acid

A solution of the blocked glycolipid (46 mg) in dry methanol (8 ml) containing sodium methoxide (3 mg) is kept for 3 hours at room temperature. The medium is adjusted to pH 9 by gradual addtion of 2.5 N sodium hydroxide (10 drops). The suspension is stirred for 16 hours and tetrahydrofuran (20 ml) is added to dissolve the precipitates. The solution is de-ionized with acidic resin, filtered, and concentrated to dryness. The residue is triturated with ethyl ether-petroleum ether to give the title compound (30 mg, 80% yield).

EXAMPLE 9

An aqueous suspension of the final product of Example 1 in phosphate buffered saline (PBS) is sterile filtered and added in levels of 0.005 mg and 0.05 mg to 2 samples of bivalent whole influenza vaccine (A Victoria and B Hong Kong strains). Similar adjuvant vaccine preparations are prepared using the final products of examples 2-8.

What is claimed is:

1. A compound selected from the group consisting of:
6-(5-cholesten-3β-yloxy)hexyl 1-thio-β-L-fucopyranoside;
6-(5-cholesten-3β-yloxy)hexyl 1-thio-β-D-glucopyranoside;
6-(5-cholesten-3β-yloxy)hexyl 2-acetamido-2-deoxy-1-thio-β-D-glucopyranoside;

6-(5-cholesten-3β-yloxy)hexyl 2-acetamido-2-deoxy-1-thio-β-D-galactopyranoside;

6-(5-cholesten-3β-yloxy)hexyl 1-thio-β-D-xylopyranoside;

6-(5-cholesten-3β-yloxy)hexyl 1-thio-α-L-arabinopyranoside;

6-(5-cholesten-3β-yloxy)hexyl 1-thio-β-lactoside, and

2-S-[6-(5-cholesten-3β-yloxy)hexyl]-2-thio-β-D-N-acetylneuraminic acid.

2. An intermediate for a compound of claim 1 selected from the group consisting of 6-(5-cholesten-3β-yloxy)hexyl 2,3,4-tri-O-acetyl-1-thio-β-L-fucopyranoside;

6-(5-cholesten-3β-yloxy)hexyl 2,3,4,6-tetra-O-acetyl-1-thio-β-D-glucopyranoside;

6-(5-cholesten-3β-yloxy)hexyl 2-acetamido-3,4,6,-tri-O-acetyl-2-deoxy-1-thio-β-D-glucopyranoside;

6-(5-cholesten-3β-yloxy)hexyl 2-acetamido-3,4,6-tri-O-acetyl-2-deoxy-1-thio-β-D-galactopyranoside;

6-(5-cholesten-3β-yloxy)hexyl 2,3,4-tri-O-acetyl-1-thio-β-D-xylopyranoside;

6-(5-cholesten-3β-yloxy)hexyl 2,3,4-tri-O-acetyl-1-thio-α-L-arabinopyranoside;

6-(5-cholesten-3β-yloxy)hexyl hepta-O-acetyl-1-thio-β-lactoside;

6-(5-cholesten-3β-yloxy)-hexane-1-thiol, and

Methyl 4,7,8,9-tetra-O-acetyl-N-acetyl-2-S-[6-(5-cholesten-3β-yloxy)hexyl]2-thio-D-neuraminate.

3. A composition comprising an antigenic material and a compound of claim 1.

4. A composition according to claim 3 wherein the compound is present in an amount effective to exert an adjuvant effect.

* * * * *